(12) United States Patent
Yu

(10) Patent No.: US 7,094,958 B2
(45) Date of Patent: Aug. 22, 2006

(54) RICE α-AMYLASE TRANSCRIPTIONAL ENHANCERS

(75) Inventor: Su-May Yu, Taipei (TW)

(73) Assignee: Academia Sinica, Taipei (TW)

( * ) Notice: Subject to any disclaimer, the term of this patent is extended or adjusted under 35 U.S.C. 154(b) by 326 days.

(21) Appl. No.: 10/060,515

(22) Filed: Jan. 30, 2002

(65) Prior Publication Data
US 2003/0145357 A1    Jul. 31, 2003

(51) Int. Cl.
| | |
|---|---|
| *C12N 15/11* | (2006.01) |
| *C12N 15/63* | (2006.01) |
| *C12N 15/82* | (2006.01) |
| *A01H 5/00* | (2006.01) |

(52) U.S. Cl. .................. 800/320.2; 800/284; 800/287; 800/298; 800/320; 435/320.1; 435/419

(58) Field of Classification Search ................ 800/284, 800/287, 298, 320.2, 320; 536/23.1, 24.1; 435/320.1, 419
See application file for complete search history.

(56) References Cited

U.S. PATENT DOCUMENTS 5,917,029 A * 6/1999 Yu ............................ 536/24.1

OTHER PUBLICATIONS

Chen P. et al. Journal of Biological Chemistry, Apr. 19, 2002; vol. 277, No. 16; pp. 13641-13649.*
Lanahan M. et al. The Plant Cell, Feb. 1992; vol. 4 pp. 203-211.*
Lu C. et al. The Journal of Biological Chemistry, Apr. 24, 1998; vol. 273, No. 17, pp. 10120-10131.*
Chung-An Lu, et al. *Sugar Response Sequence in the Promoter of a Rice α-Amylase Gene Serves as a Transcriptional Enhancer*. The Journal of Biological Chemistry, vol. 273, No. 17, Apr. 24, 1998, pp. 10120-10131.

* cited by examiner

*Primary Examiner*—Russell P. Kallis
(74) *Attorney, Agent, or Firm*—Fish & Richardson P.C.

(57) ABSTRACT

A recombinant nucleic acid containing a transcriptional enhancer from a rice αAmy8 gene, a promoter operably linked to the enhancer, and a coding sequence operably linked to the promoter and encoding a transcript. Also disclosed is a stably transformed plant cell or a transgenic plant containing a recombinant nucleic acid described above, or a similar recombinant nucleic acid with a plurality of a rice αAmy3 enhancer.

26 Claims, No Drawings

RICE α-AMYLASE TRANSCRIPTIONAL ENHANCERS

BACKGROUND

Various strategies have been employed to increase the activity of promoters in transgenic plants. One of the strategies is to use an enhancer that increases the transcriptional activity of a promoter, either homologous or heterologous to the enhancer. This strategy is useful in producing transgenic plants over-expressing endogenous or exogenous genes that control agronomically important traits or over-production of biomolecules.

SUMMARY

This invention relates to rice α-amylase gene enhancers which can be used to increase the promoter activity in a transformed plant cell or in a transgenic plant.

In one aspect, the invention features a recombinant nucleic acid that contains a transcriptional enhancer from a rice αAmy8 gene; a promoter, heterologous to the enhancer, operably linked to the enhancer; and a coding sequence operably linked to the promoter and encoding a transcript. The transcript can encode a polypeptide, or can be an RNA that interferes with the function of another RNA (e.g., mRNA, transfer RNA, ribosomal RNA, and small nucleolar RNA) in a plant cell such as a monocot (e.g., a cereal).

One example of a rice αAmy8 gene enhancer is SEQ ID NO: 1, i.e., bp −318 to −89 of αAmy8, as shown below:

```
                                            (SEQ ID NO:1)
CGTCATGCGTGATCGGTGATCGATCACCGAGAGAGACCGGACGACGAGTC
GAGAGAGCTCGCGCCGCCTCGATCGGCGCGGCGGTGACTCGAGCAGGGCC
TGAAGTAGCTGCACGGCTCAAGGCGGCACTCCATCACCGGACACCGGGGT
CCAGACTACTCGTTTCCGTTGGAGAAATAACCACCTTTATCCATGTTGCT
TATCCGTGAATTGCAACAGCATTGATTGTT.
```

In another aspect, the invention features a recombinant nucleic acid that contains a plurality of a transcriptional enhancer (e.g., 2, 3, or 4 copies) from a rice αAmy8 gene; a promoter, either homologous or heterologous to the enhancer, operably linked to the enhancer; and a coding sequence operably linked to the promoter and encoding a transcript.

The recombinant nucleic acids of this invention can be introduced into a plant cell to generate a stably transformed cell, which can further be cultivated to generate a transgenic plant. Such stably transformed plant cells and transgenic plants are both within the scope of the invention.

Also within the scope of this invention is a stably transformed plant cell or a transgenic plant containing a recombinant nucleic acid that includes a plurality of a transcriptional enhancer from a rice αAmy3 gene; a promoter, either homologous or heterologous to the enhancer, operably linked to the enhancer; and a coding sequence operably linked to the promoter and encoding a transcript.

Examples of a rice αAmy3 gene enhancer include SEQ ID NO:2 (bp −186 to −82 of αAmy3), SEQ ID NO:3 (bp −133 to −82 of αAmy3), and SEQ ID NO:4 (bp −186 to −122 of αAmy3), as shown below:

```
                                            (SEQ ID NO:2)
ATCCCGTCGCCTTGGAGACCGGGCCCCGACGCGGCCGACGCGGCGCCTAC
GTGGCCATGCTTTATTGCCTTATCCATATCCACGCCATTTATTGTGGTCG
TCTCT,
```

```
                                            (SEQ ID NO:3)
GCCATGCTTTATTGCCTTATCCATATCCACGCCATTTATTGTGGTCGTCT
CT, and
```

```
                                            (SEQ ID NO:4)
ATCCCGTCGCCTTGGAGACCGGGCCCCGACGCGGCCGACGCGGCGCCTAC
GTGGCCATGCTTTAT.
```

Sequences longer or shorter than SEQ ID NO:1 (e.g., bp −200 to −89 of αAmy8; "SEQ ID NO:7") can also be used as enhancers, as long as they exhibit enhancer activity as determined by the methods described in the examples below or by analogous methods. Sequences with nucleic acid variations, e.g., due to polymorphism or as a result of recombinant genetic manipulation, can also be used as enhancers. For instance, a modified αAmy8 enhancer with a duplication of the TATCCA element increases the enhancer activity by 6-fold in rice embryos. Indeed, also contemplated within the scope of this invention are recombinant nucleic acids, stably transformed plant cells, and transgenic plants containing such sequence variants that retain the enhancer activity.

The details of some embodiments of the invention are set forth in the description below. Other features, objects, and advantages of the invention will be apparent from the description, and from the claims.

DETAILED DESCRIPTION

This invention relates to rice α-amylase gene enhancers which can be used to increase the promoter activity in a transformed plant cell or in a transgenic plant.

α-Amylases are the major amylolytic enzymes for hydrolysis of starch stored in the endosperm during germination of cereal grains, providing the nutrients needed for the growth of the germ. Expression of α-amylase genes in cereals is induced by both gibberellin (GA) and sugar starvation. Rice α-amylase isozymes are encoded by at least nine genes (Thomas, B. R., and Rodriguez, R. L. (1994) *Plant Physiol* 106: 1235–1239), among which αAmy3 and αAmy8 are highly inducible by sugar starvation. A 105-bp sugar response sequence (SRS), SEQ ID NO:2 (shown above), was previously identified in αAmy3 (Lu et al. (1998) *J Biol Chem* 273: 10120–10131).

Here, a 230-bp sequence (SEQ ID NO:1; shown above) in a rice αAmy8 gene is found to enhance the activity of a promoter in a plant cell. This enhancer is located at bp −318 to −89 of αAmy8, and contains a 31-bp GC box at positions −266 to −236 and a TATCCA element at positions −131 to −126 upstream of the transcriptional start site, both of which are conserved in αAmy3 SRS (i.e., SEQ ID NO:2). It also contains a sequence homologous to the c-Myb-binding site (Nakagoshi et al. (1990) *J Biol Chem* 265: 3479–3483) and a GA response sequence (GARS) (Gubler et al. (1999) *Plant J* 17: 1–9), neither of which is present in αAmy3 SRS. This 230-bp αAmy8 enhancer and its variants are thus designated as αAmy8 SRS/GARS.

Sequences longer or shorter than SEQ ID NO:1 (e.g., bp −200 to −89 of αAmy8) can also be used as enhancers, as long as they exhibit enhancer activity as determined by the methods described in the examples below or by analogous methods. Sequences with nucleic acid variations, e.g., due to polymorphism or as a result of recombinant genetic manipulation, can also be used as enhancers. For instance, a modified αAmy8 enhancer with a duplication of the TATCCA element increases the enhancer activity by 6-fold in rice embryos. Indeed, also contemplated within the scope of this invention are recombinant nucleic acids, stably transformed plant cells, and transgenic plants containing such sequence variants that retain the enhancer activity.

Thus, this invention features a recombinant nucleic acid containing a transcriptional enhancer from a rice αAmy8 gene (i.e., αAmy8 SRS/GARS), which can be used to generate a transformed cell and a transgenic plant. The recombinant nucleic acid of the invention can be a nucleic acid fragment containing a transcriptional enhancer from a rice αAmy8 gene; a promoter, heterologous to the enhancer, operably linked to the enhancer; and a coding sequence operably linked to the promoter and encoding a transcript. It can also be a plasmid or virus vector that contains the just-described nucleic acid fragment.

The transcript can be an RNA that interferes with the function of another RNA in a plant cell, for example, preventing an mRNA from being translated into a polypeptide, or triggering specific RNA degradation to facilitate targeted post-transcriptional gene silencing (Mol et al. (1990) FEBS Lett 268(2): 427–30 and Fire et al. (1998) Nature 391: 806–811). Alternatively, the transcript can encode a polypeptide, either needed for the improvement of certain traits of a transgenic plant, or for over-production of the polypeptide in transformed plant cells or a transgenic plant. To facilitate recovery of the over-produced polypeptide, a sequence encoding a signal peptide can be integrated into an above-described recombinant nucleic acid at an appropriate position, e.g., between the promoter and the coding sequence for the polypeptide. As a result, the polypeptide is secreted into the cell culture medium or into the endosperm of germinated seeds, thereby facilitating its recovery.

As an αAmy8 SRS/GARS enhancer increases the promoter activity in a dose-dependent manner, it is preferred that the recombinant nucleic acid contain a plurality of a transcriptional enhancer (e.g., 2, 3, or 4 copies) from a rice αAmy8 gene; a promoter, either homologous or heterologous to the enhancer, operably linked to the enhancer; and a coding sequence operably linked to the promoter and encoding a transcript.

When multiple copies of an enhancer are used, they need not be placed in the same orientation in relation to each other. Also, an intervening sequence (e.g., 50–100 bp in length or longer) can be present between two copies of an enhancer, provided it does not interfere with the enhancer function. Typically, if too many copies (e.g., more than 4 copies) of an enhancer are used, they may be spiced out from a vector through recombination when the vector is replicated in bacteria. In addition, too many copies of an enhancer may cause gene silencing in transgenic plants. Therefore, although the promoter activity is increased proportionally to the copy number of an enhancer in general, the actual maximal copy number of an enhancer can be determined by the methods described in the experiments below or by analogous methods.

The promoter used in a recombinant nucleic acid of this invention can be ubiquitously active, such as that derived from an actin gene, cauliflower mosaic virus 35S ("CaMV35S") RNA, or a ubiquitin gene; or can be inducible, such as that derived from an α-amylase (e.g., a rice αAmy3, αAmy6, αAmy7, αAmy8, or αAmy10 gene, which is sugar-responsive; see U.S. Pat. No. 5,460,952), invertase, sucrose synthase, patatin, β-amylase, sporamin, or photosynthetic gene. Additional transcription regulatory elements such as other enhancers can also be included in a recombinant nucleic acid of the invention to highly activate and tightly regulate the promoter activity.

A recombinant nucleic acid of this invention (e.g., a recombinant nucleic acid containing a transcriptional enhancer from a rice αAmy8 gene) can be introduced into a plant cell to generate a stably transformed cell, which can further be cultivated to generate a transgenic plant. Such stably transformed plant cells and transgenic plants are both within the scope of the invention.

Also within the scope of this invention is a stably transformed plant cell or a transgenic plant containing a recombinant nucleic acid that includes a plurality of a transcriptional enhancer from a rice αAmy3 gene; a promoter, either homologous or heterologous to the enhancer, operably linked to the enhancer; and a coding sequence operably linked to the promoter and encoding a transcript. Examples of a rice αAmy3 gene enhancer include SEQ ID NO:2 (bp −186 to −82 of αAmy3), SEQ ID NO:3 (bp −133 to −82 of αAmy3), and SEQ ID NO:4 (bp −186 to −122 of αAmy3).

αAmy3 SRS (e.g., SEQ ID NO:2, 3, or 4) enhances the promoter activity in sugar-starved rice protoplasts (Lu et al. (1998) *J Biol Chem* 273: 10120–10131). Unexpectedly, in stably transformed rice suspension cells, αAmy3 SRS significantly increases the promoter activity regardless of whether the cells are cultured with or without a supply of sugar. The promoter activity is also much higher in a stably transformed cell than in a protoplast transient expression system.

Both αAmy3 SRS and αAmy8 SRS/GARS enhance the promoter activity in transgenic rice. Yet, αAmy3 SRS enhances the promoter activity in a tissue-independent manner, while αAmy8 SRS/GARS enhances the promoter activity mainly in the endosperm and embryo of germinated rice seeds. In addition, the enhancer activity of αAmy8 SRS/GARS is subject to sugar repression and GA induction in rice embryos, the sugar repression overriding GA induction. Thus, αAmy3 SRS and αAmy8 SRS/GARS are useful for regulated expression of endogenous or exogenous genes in a stably transformed plant cell or a transgenic plant.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLES

Experimental Procedures (1) Plant Material

The rice variety used in these examples was *Oryza sativa* L. cv. Tainung 67. Immature seeds were dehulled, sterilized with 3% NaOCl for 30 min, washed extensively with sterile water, and placed on N6D agar medium (Toki, S. (1997) *Plant Mol Biol Rep* 5: 16–21) for callus induction. After one month, calli derived from scutellum were subcultured in fresh N6D medium for transformation.

(2) Plasmid Construction

For construction of a plasmid containing an Act1-Luc chimeric gene, an EcoRI site in the multiple cloning sites of pBluescript SKII+ (Stratagene) was first removed by digestion with EcoRI, and then blunt-ended and religated. The rice Act1 5' region (including a 1.4-kb 5'-flanking sequence, a 79-bp 5' noncoding exon, a 447-bp 5' intron, and a 25-bp first coding exon) was excised from pDM302 (Cao et al. (1992) *Plant Cell Rep* 11: 586–591) with HindIII and subcloned into the same site in pBluescript which lacks the EcoRI site to generate pAct. Rice αAmy3 SRS (−186 to −82 relative to the transcriptional start site of αAmy3) was PCR-amplified using oligonucleotides 5'-CCCGAAT-TCATCCCGTCGCCTTGGAGA-3' (SEQ ID NO:5, EcoRI site underlined) as the 5' primer and 5'-CCCGAATTCA-GAGACGACAATAAT-3' (SEQ ID NO:6, EcoRI site underlined) as the 3' primer and p3G-132II (Lu et al. (1998) *J Biol Chem* 273: 10120–10131), which contains a 1.7-kb 5' region of αAmy3, as the DNA template. The DNA fragment containing the SRS was digested with EcoRI and inserted into an EcoRI site (−459 relative to the transcriptional start site) of the Act1 promoter in three tandem repeats in the same orientation as the promoter to generate pACT-3SRS. A SalI-BglII fragment containing a fusion sequence of the Luc coding sequence-Nos terminator was excised form pJD312 (Luehrsen et al. (1992) *Methods Enzymol* 216: 397–414), blunt-ended, and inserted into a SmaI site of pAct and pAct-3SRS to generate pB-Act-LN and pB-Act-3SRS-LN. pB-Act-LN and pB-Act-3SRS-LN were linearized with PstI and inserted into the same site in a binary vector pSMY1H (Ho et al. (2000) *Plant Physiol* 122: 57–66), which contains a fusion gene of the 35S promoter-Hph coding region-tumor morphology large gene (Tml) terminator, thereby generating pAct-LN and pAct-3SRS-LN.

(3) Transformation of Rice

Plasmids pAct-LN and pAct-SRS-LN were introduced into *A. tumefaciens* strain EHA101 (Hood et al. (1986) *J Bacteriol* 168: 1291–1301) with an electroporator (BTX, San Diego) according to the manufacturer's instructions. Calli induced from immature rice seeds were co-cultured with *A. tumefaciens* and putative transgenic plants were regenerated from calli according to the methods described by Hiei et al. (*Plant J* 6: 271–282, 1994) and Toki (*Plant Mol Biol Rep* 5: 16–211997).

(4) Suspension Cell Culture

Transformed calli were propagated as previously described by Yu et al. (*J Biol Chem* 266: 21131–21137, 1991). Established suspension cells were subcultured as previously described by Lu et al. (*J Biol Chem* 273: 10120–10131, 1998).

(5) Luciferase Activity Assay

Total proteins were extracted from cultured suspension cells or plant tissues with a CCLR buffer (100 mM $KH_2(PO_4)$, pH 7.8, 1 mM EDTA, 10% glycerol, 1% Triton X-100, 7 mM β-mercapatoethanol), and the protein concentration was determined with a Coomassie protein assay reagent (Pierce). Luciferase activity assay was performed as previously described (Lu et al. (1998) *J Biol Chem* 273: 10120–10131).

Example 1

αAmy8 SRS/GARS Enhanced Act1 Promoter Activity in Transgenic Rice

An αAmy8 SRS/GARS enhancer, which encompasses positions −318 to −89 of the αAmy8 promoter, was inserted at position −459 of the Act1 promoter in three tandem repeats and in the same orientation as the promoter, and tested for its effect on the Act1 promoter activity in transgenic rice.

Transformed calli carrying Act1-Luc and Act1-8SRS/GARS-Luc chimeric genes were regenerated, self-fertilized for three generations to obtain T3 homozygous seeds. The homozygosity of transgenic seeds was determined by germination of 25 transgenic seeds in water containing 50 g/ml hygromycin for 7 days and calculation of the ratio of the number of growing seedlings to the number of non-growing seedlings. Theoretically, seeds of a transgenic line homozygous for a trans-gene should all germinate and grow under these conditions.

T3 homozygous seeds of transgenic lines Act 6-9-1 and Act(8SRS/GARS) 5 were germinated and grown for 8 days. Various tissues of seedlings were collected and assayed for luciferase activity. Unexpectedly, the αAmy8 SRS/GARS enhancer increased the Act1 promoter activity mainly in endosperms and embryos of germinated seeds and seedlings.

The αAmy8 SRS/GARS enhancer was also fused upstream of a CaMV35S minimal promoter-Luc fusion gene, which was then introduced into the rice genome. Several transgenic rice lines were obtained, and the T2 seeds of one randomly selected line, T4–12, were germinated for 6 days. Various tissues of germinated seeds were collected and assayed for luciferase activity. The luciferase activity in endosperms and embryos was found 74- and 20-fold of that in roots, respectively, while the luciferase activity in shoots was similar to that in roots. These findings show that the αAmy8 SRS/GARS enhancer confers endosperm- and embryo-specific activity to a minimal promoter in germinated transgenic rice seeds.

In a second experiment, the same batch of T2 seeds from transgenic lines T4–12 described above was pretreated with 2,4-D for 8 days. Embryos were collected and divided into four groups. Each group of embryos was incubated with or without sucrose and with or without GA for 2 days, and assayed for luciferase activity. In the presence of sucrose, the luciferase activity in embryos was relatively low regardless of whether GA was present or not. In the absence of both sucrose and GA, the luciferase activity in embryos increased significantly by 5.5-fold. Addition of GA in the absence of sucrose enhanced the luciferase activity by 8.2-fold.

In a third experiment, embryos of T1 seeds from transgenic line T4–12 were removed in order to cut-off the source of GA. The endosperms were then divided into four groups. Each group of endosperms was incubated with or without sucrose and with or without GA for 2 days, and assay for luciferase activity. In the absence of GA, the luciferase activity in endosperms was low regardless of whether sucrose was present or not. In the presence of both GA and sucrose, the luciferase activity in endosperms increased by 4-fold. Removal of sucrose in the presence of GA did not alter the luciferase activity. These results demonstrate that the αAmy8 SRS/GARS enhancer confers GA responsiveness to a minimal promoter in both rice embryos and endosperms.

Example 2

αAmy3 SRS Enhanced Act1 Promoter Activity in Stably Transformed Rice Suspension Cells The firefly luciferase gene (Luc) was fused downstream of the Act1 promoter or the Act1 promoter containing 3 tandem repeats of αAmy3 SRS to generate Act1-Luc and Act1-3SRS-Luc. The resulted chimeric genes were introduced into the rice genome via *Agrobacterium*-mediated transformation. Several transformed cell lines were obtained, and four lines for each construct were randomly selected for further studies.

The transformed calli were cultured as suspension cells. These cells were then cultured in medium with or without sucrose for 2 days prior to being subjected to a luciferase activity assay. The luciferase activity conferred by the wild type Act1 promoter was very low in sucrose-starved cells. It was 6- to 8-fold less than the luciferase activity in sucrose-provided cells. By contrast, the luciferase activity conferred by the Act1-3SRS promoter increased dramatically in sucrose-starved cells to approximately 2–5.5 folds of that in sucrose-provided cells. Unexpectedly, the Act1-3SRS promoter conferred significantly higher luciferase activity regardless of whether the cells were cultured with or without a supply of sucrose, i.e., αAmy3 SRS enhanced the Act1 promoter activity by an average of 3-fold in sucrose-provided cells and by at least 20-fold in sucrose-starved cells. These results indicate that, in stably transformed rice suspension cells, expression of luciferase is significantly enhanced by integration of αAmy3 SRS into the Act1 promoter. Additionally, αAmy3 SRS converts the sugar-inducible Act1 promoter into a sugar starvation-inducible promoter.

Example 3

αAmy3 SRS Enhanced Act1 Promoter Activity in Transgenic Rice

T3 homozygous seeds of four transgenic lines carrying Act1-Luc and eight transgenic lines carrying Act1-3SRS-Luc were germinated and grown for 8 days. Leaves were collected from seedlings and assayed for luciferase activity. The luciferase activity was not significantly different in the leaves of all transgenic lines carrying the same construct. The average luciferase activity conferred by the Act1-3SRS promoter in different transformants was similar: approximately 2.5- to 3-fold higher than that conferred by the Act1 promoter. These results indicate that αAmy3 SRS generally enhances the Act1 promoter activity in transgenic rice.

Unexpectedly, the enhancement of the Act1 promoter activity by αAmy3 SRS was developmentally regulated. T3 homozygous seeds of transgenic lines Act 6-9-1 and Act (3SRS) 5-15-1 were germinated and grown for a certain period of time. The Act1-3SRS promoter conferred higher luciferase activity than the Act1 promoter in various tissues of germinating seeds and seedlings after two weeks. The difference in the enhancement of the luciferase activity was most dramatic in roots (5- to 56-fold) and next in shoots (4- to 11-fold) and embryos (3- to 18-fold). The luciferase activity in various organs conferred by both the Act1 and Act1-3SRS promoters peaked within 7–8 days after germination and declined thereafter. Within eight weeks of growth, the difference in the enhancement of the luciferase activity was highest in roots (7- to 38-fold), next highest in leaves (5- to 20-fold), and lowest in sheaths (4- to 7-fold).

Total luciferase activities in leaves, sheaths, and roots of transgenic seedlings and plants were calculated and compared. The luciferase activity in transgenic rice, conferred by either the Act1 or Act1-3SRS promoter, fluctuated in a developmental stage-dependent manner. The luciferase activity in various tissues reached its first peak within 1 week after germination, reached its lowest level at week 2 or 3, and rose again at week 4.

Further, the luciferase activity conferred by the Act1-3SRS promoter was significantly higher than that conferred by the Act1 promoter, regardless of whether seedlings were grown in dark or under a light/dark cycle. Expression of luciferase in leaves of seedlings grown under light/dark cycles was also higher than in leaves grown in dark within the first week after germination regardless of whether or not the Act1 promoter contained the αAmy3 SRS.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A recombinant nucleic acid comprising:
a transcriptional enhancer from a rice αAmy8 gene, the enhancer containing a gibberellin response sequence;
a promoter operably linked to the enhancer, the promoter being heterologous to the enhancer; and
a coding sequence operably linked to the promoter and encoding a transcript, wherein the transcriptional enhancer contains SEQ ID NO: 1 or a complement thereof.

2. The nucleic acid of claim 1, wherein the transcript encodes a polypeptide.

3. The nucleic acid of claim 1, wherein the transcriptional enhancer is SEQ ID NO:1.

4. A recombinant nucleic acid comprising:
a plurality of a transcriptional enhancer from a rice αAmy8 gene, the enhancer containing a gibberellin response sequence,
a promoter operably linked to the enhancer, and
a coding sequence operably linked to the promoter and encoding a transcript, wherein the transcriptional enhancer contains SEQ ID NO: 1 or a complement thereof.

5. The nucleic acid of claim 4, wherein the nucleic acid comprises 2, 3, or 4 copies of the enhancer.

6. The nucleic acid of claim 5, wherein the transcript encodes a polypeptide.

7. The nucleic acid of claim 5, wherein the transcriptional enhancer is SEQ ID NO:1.

8. The nucleic acid of claim 4, wherein the transcript encodes a polypeptide.

9. The nucleic acid of claim 4, wherein the transcriptional enhancer is SEQ ID NO:1.

10. A stably transformed plant cell or a transgenic plant, comprising a recombinant nucleic acid containing:
   a transcriptional enhancer from a rice αAmy8 gene, the enhancer containing a gibberellin response sequence;
   a promoter operably linked to the enhancer, the promoter being heterologous to the enhancer; and
   a coding sequence operably linked to the promoter and encoding a transcript, wherein the transcriptional enhancer contains SEQ ID NO: 1 or a complement thereof.

11. The stably transformed plant cell or the transgenic plant of claim 10, wherein the transcript encodes a polypeptide.

12. The stably transformed plant cell or the transgenic plant of claim 10, wherein the transcriptional enhancer is SEQ ID NO:1.

13. The stably transformed plant cell or the transgenic plant of claim 10, wherein the plant is a monocot plant.

14. The stably transformed plant cell or the transgenic plant of claim 13, wherein the plant is a cereal plant.

15. The stably transformed plant cell or the transgenic plant of claim 14, wherein the plant is rice.

16. A stably transformed plant cell or a transgenic plant, comprising a recombinant nucleic acid containing;
   a plurality of a transcriptional enhancer from a rice αAmy8 gene, the enhancer containing a gibberellin response sequence,
   a promoter operably linked to the enhancer, and
   a coding sequence operably linked to the promoter and encoding a transcript, wherein the transcriptional enhancer from a rice αAmy8 gene contains SEQ ID NO: 1 or a complement thereof.

17. The stably transformed plant cell or the transgenic plant of claim 16, wherein the transcriptional enhancer is SEQ ID NO:1.

18. The stably transformed plant cell or the transgenic plant of claim 16, wherein the nucleic acid comprises 2, 3, or 4 copies of the enhancer.

19. The stably transformed plant cell or the transgenic plant of claim 18, wherein the transcript encodes a polypeptide.

20. The stably transformed plant cell or the transgenic plant of claim 18, wherein the plant is a monocot plant.

21. The stably transformed plant cell or the transgenic plant of claim 20, wherein the plant is a cereal plant.

22. The stably transformed plant cell or the transgenic plant of claim 21, wherein the plant is rice.

23. The stably transformed plant cell or the transgenic plant of claim 16, wherein the transcript encodes a polypeptide.

24. The stably transformed plant cell or the transgenic plant of claim 16, wherein the plant is a monocot plant.

25. The stably transformed plant cell or the transgenic plant of claim 24, wherein the plant is a cereal plant.

26. The stably transformed plant cell or the transgenic plant of claim 25, wherein the plant is rice.

* * * * *

SEQUENCE LISTING

<160> NUMBER OF SEQ ID NOS: 7

<210> SEQ ID NO 1
<211> LENGTH: 230
<212> TYPE: DNA
<213> ORGANISM: Oryza sativa

<400> SEQUENCE: 1
cgtcatgcgt gatcggtgat cgatcaccga gagagaccgg acgacgagtc gagagagctc       60
gcgccgcctc gatcggcgcg gcggtgactc gagcagggcc tgaagtagct gcacggctca      120
aggcggcact ccatcaccgg acaccggggt ccagactact cgtttccgtt ggagaaataa      180
ccacctttat ccatgttgct tatccgtgaa ttgcaacagc attgattgtt                 230

<210> SEQ ID NO 2
<211> LENGTH: 105
<212> TYPE: DNA
<213> ORGANISM: Oryza sativa

```
<400> SEQUENCE: 2
atcccgtcgc cttggagacc gggccccgac gcggccgacg cggcgcctac gtggccatgc    60
tttattgcct tatccatatc cacgccattt attgtggtcg tctct                  105

<210> SEQ ID NO 3
<211> LENGTH: 52
<212> TYPE: DNA
<213> ORGANISM: Oryza sativa

<400> SEQUENCE: 3
gccatgcttt attgccttat ccatatccac gccatttatt gtggtcgtct ct           52

<210> SEQ ID NO 4
<211> LENGTH: 65
<212> TYPE: DNA
<213> ORGANISM: Oryza sativa

<400> SEQUENCE: 4
atcccgtcgc cttggagacc gggccccgac gcggccgacg cggcgcctac gtggccatgc    60
tttat                                                               65

<210> SEQ ID NO 5
<211> LENGTH: 27
<212> TYPE: DNA
<213> ORGANISM: Artificial Sequence
<220> FEATURE:
<223> OTHER INFORMATION: Synthetically generated primer

<400> SEQUENCE: 5
cccgaattca tcccgtcgcc ttggaga                                       27

<210> SEQ ID NO 6
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 6
cccgaattca gagacgacaa taat                                          24

<210> SEQ ID NO 7
<211> LENGTH: 112
<212> TYPE: DNA
<213> ORGANISM: Oryza sativa

<400> SEQUENCE: 7
caaggcggca ctccatcacc ggacaccggg gtccagacta ctcgtttccg ttggagaaat    60 aaccacctttt atccatgttg cttatccgtg aattgcaaca gcattgattg tt          112
```